United States Patent [19]

Chiang et al.

[11] Patent Number: 5,713,938
[45] Date of Patent: Feb. 3, 1998

[54] FUZZY LOGIC EXPERT SYSTEM FOR AN IMPLANTABLE CARDIAC DEVICE

[75] Inventors: Chih-ming James Chiang, Highlands Ranch, Colo.; Daniel Cooper, Hauguenau, France; Saul E. Greenhut, Aurora, Colo.

[73] Assignee: Pacesetter, Inc., Sylmar, Calif.

[21] Appl. No.: 748,127

[22] Filed: Nov. 12, 1996

[51] Int. Cl.$^6$ .................. A61N 1/37; A61B 5/0452
[52] U.S. Cl. ................................ 607/32; 128/697
[58] Field of Search ..................... 607/32; 128/697, 128/699, 702, 703, 704, 705, 708; 364/413.06

[56] References Cited

U.S. PATENT DOCUMENTS

| | | |
|---|---|---|
| 4,730,259 | 3/1988 | Gallant . |
| 4,825,869 | 5/1989 | Sasmor . |
| 4,872,122 | 10/1989 | Altschuler et al. . |
| 5,265,010 | 11/1993 | Evans-Paganelli et al. . |
| 5,276,612 | 1/1994 | Selker . |
| 5,277,188 | 1/1994 | Selker . |
| 5,312,443 | 5/1994 | Adams et al. ............... 128/705 |
| 5,357,976 | 10/1994 | Feng . |
| 5,441,523 | 8/1995 | Nappholz . |

OTHER PUBLICATIONS

Expert System and Diagram for Troubleshooting Dual Chamber Pacemakers, Walter H. Olson, Michael V. McConnell, Robert L. Sah, Peter I. Hong; 1985 IEEE, pp. 53–58.

Calvin: An Expert System to Improve Arrhythmia Detector Performance in Noise, Roger G. Mark, Ramesh Patil, and George Moody; Journal of Electrocardiology, Supplemental Issue 1988, p.S117.

NASPE Abstracts, Apr. 1992, Part II, PACE, vol. 15, p.510.

*Primary Examiner*—Scott Getzow
*Attorney, Agent, or Firm*—Gottlieb, Rackman & Reisman

[57] ABSTRACT

A diagnostic device makes use of knowledge based rule system for making a prognosis of a cardiac malfunction based on operation parameters and/or patient characteristics received from a cardiac implant. The device generates a symptoms vector from the information received from the implant, and using the expert rules to generate an appropriate prognosis. Both pathological problems and programming problems may be detected in this manner.

7 Claims, 8 Drawing Sheets

Implementation

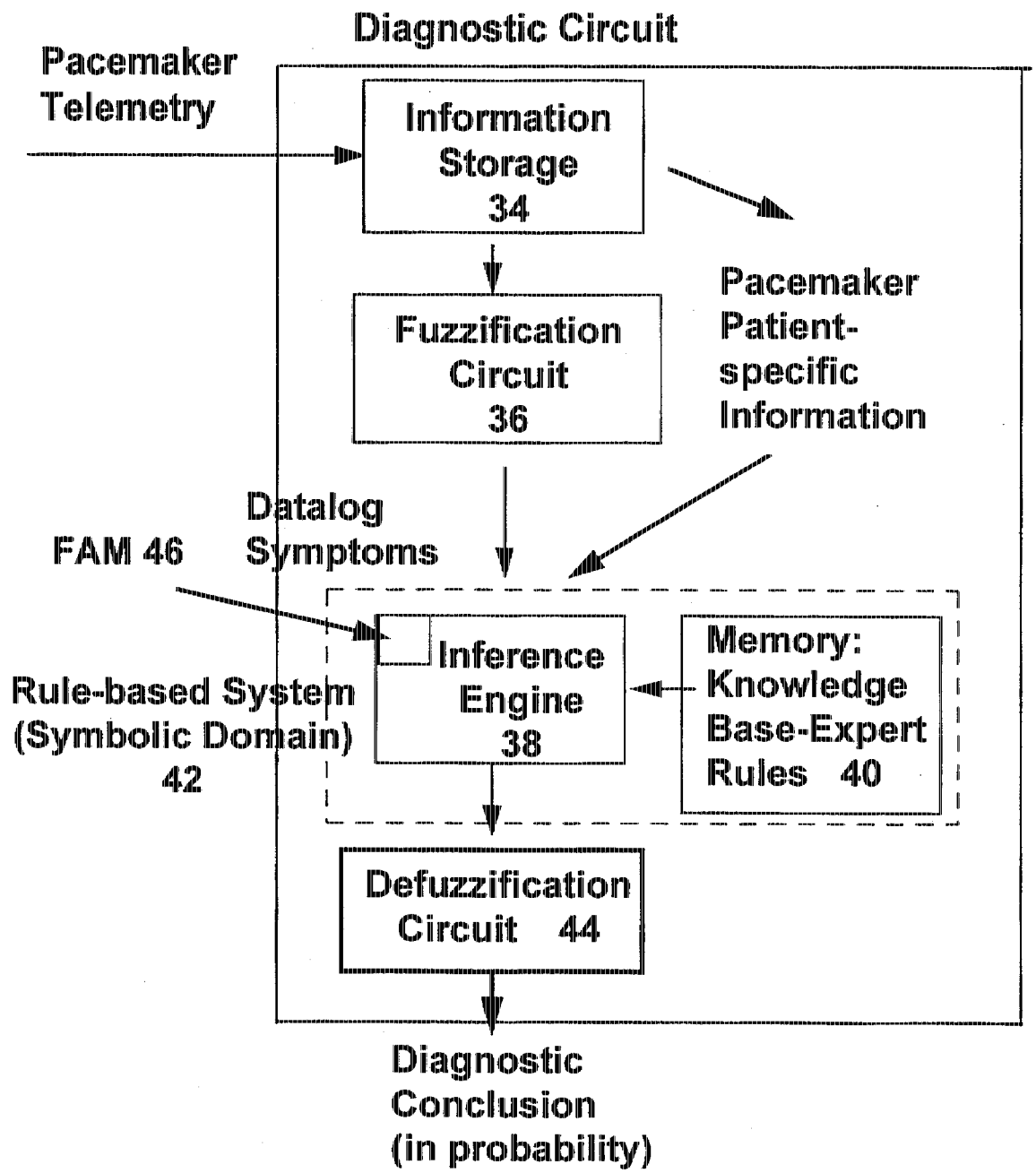

Figure 4 Fuzzification
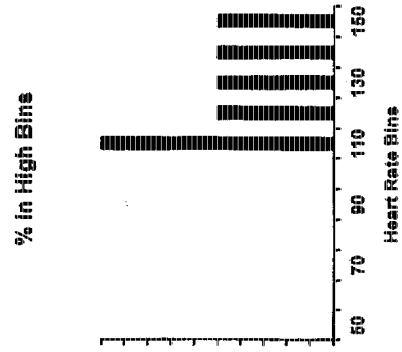
Fig 4A
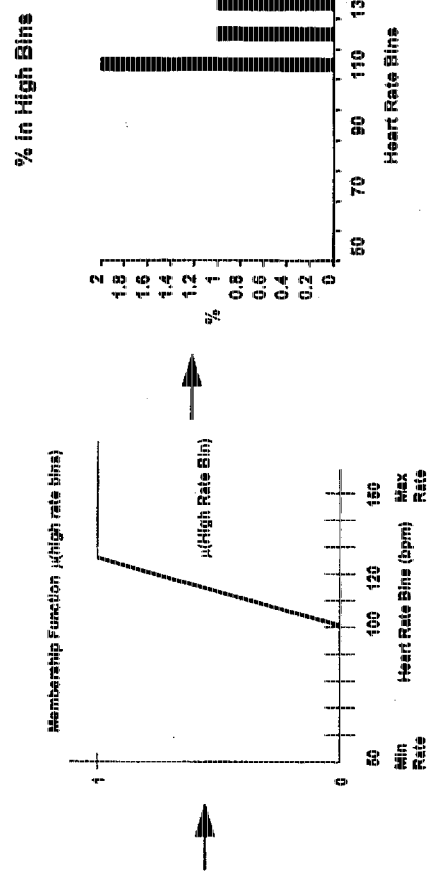
Fig 4B
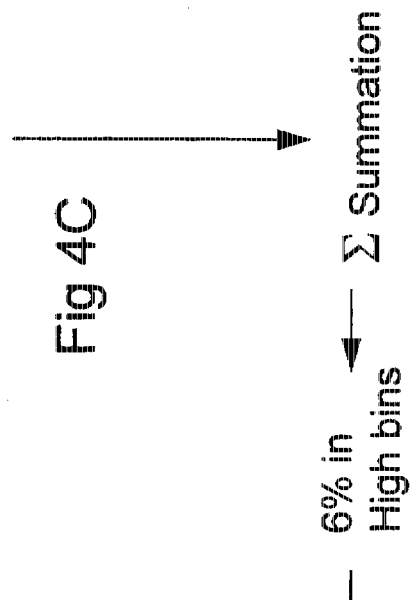
Fig 4C
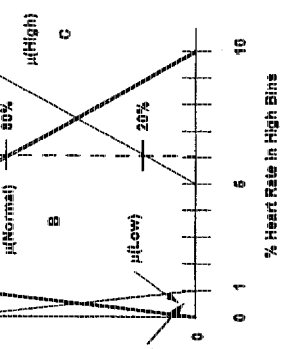
6% in High bins
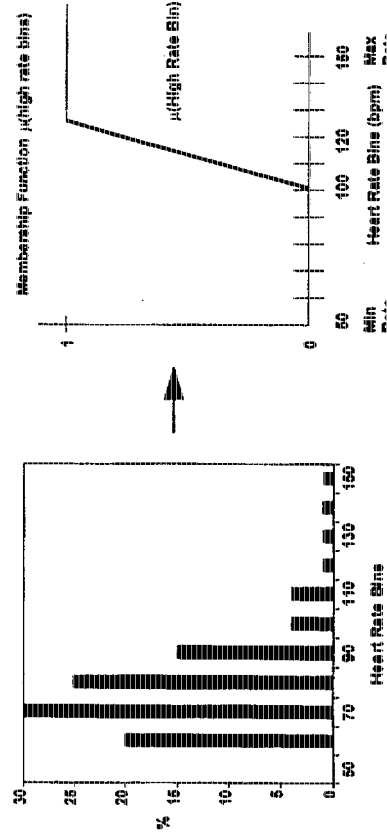
Fig 4D
20% Rate High
80% Rate Normal

Figure 7
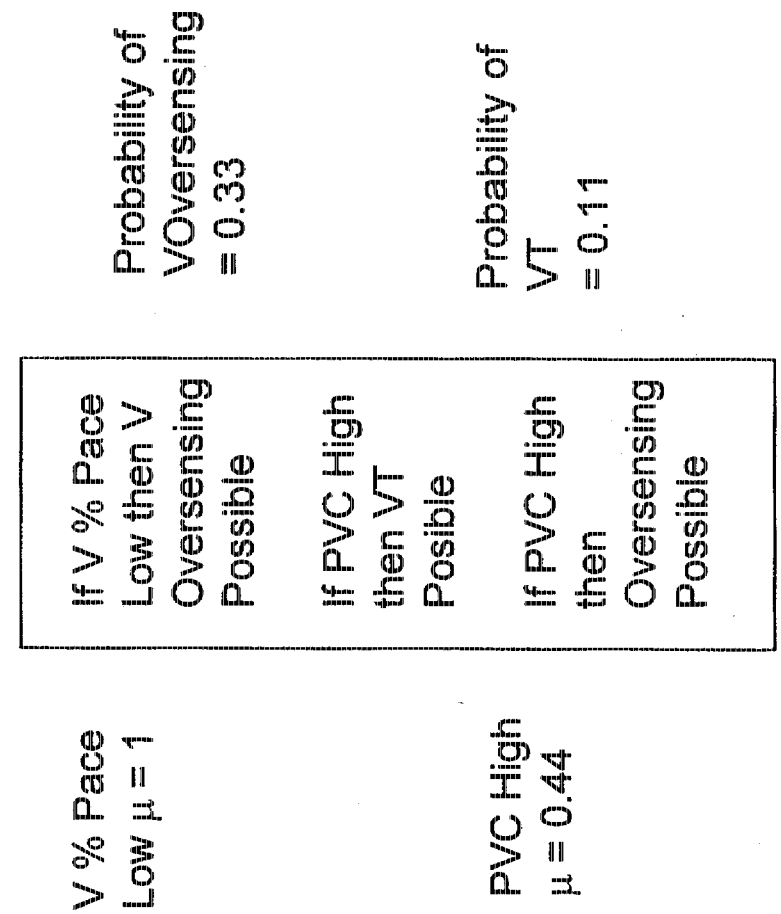
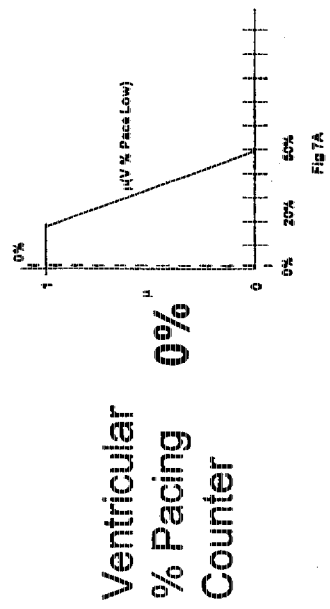
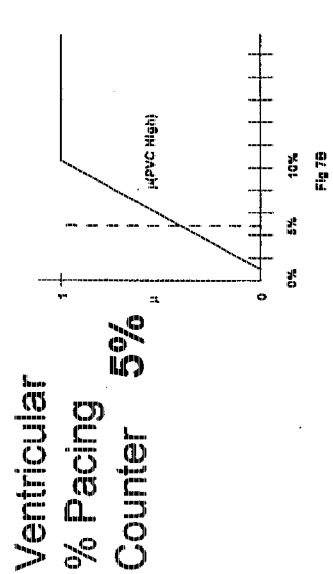

FUZZY LOGIC EXPERT SYSTEM FOR AN IMPLANTABLE CARDIAC DEVICE

BACKGROUND OF THE INVENTION

1. Field of The Invention

The invention presents a novel system for processing telemetry data obtained by implantable cardiac stimulating devices. Preferably, the system analyzes said telemetry data using fuzzy logic methodology to evaluate implantable device function.

2. Description of the Prior Art

As the therapy and other options available with implantable pacemakers increase with advancing technology, selecting the correct programmable parameters to optimize patient conditions has become more complicated. Continually evolving patient therapies, such as the development of atrial tachyarrhythmias, could also render choices for programmable parameters made at implant inadequate in responding to changing physiologic conditions.

Telemetry of stored data inside the pacer/implantable device (data logging) is an important means to determine and enhance the effectiveness of selected parameters in pacemakers following implant. Unfortunately, as more data is stored and telemetered to a programmer, it becomes quite cumbersome for the clinician to analyze, understand and assess all the data received from the pacemaker telemetry, especially since the clinician may not have the training required to perform a complete clinical analysis.

Therefore, as an aid to clinicians during follow-up of implantable devices, it would be useful to have the programmer automatically interpret and warn the clinician of any unusual results from the stored information inside the pacemaker and to provide an expert analysis of the data.

Moreover, it is time consuming for the clinician to look at all the stored and telemetered data from advanced implantable devices. Some of previous inventions in the analysis area concentrated on strictly ECG analysis. The only other method with some analysis (See U.S. Pat. No. 4,825,869 to Sasmor et. al.) did not utilize fuzzy logic to translate the data. None of the systems discussed above were implemented and, to date, clinicians have limited assistance for the interpretation of logged data.

This invention presents a system for automatic interpretation of logged data using a combined fuzzy logic expert system. As far as the present inventors know, there has been no system that uses fuzzy logic to analyze heart-device interaction.

OBJECTIVES AND SUMMARY OF THE INVENTION

In view of the above, it is an objective of the present invention to provide a programmer with analyzing capabilities for transferring data from a cardiac implant and for deriving from the said data information useful to the clinician for diagnosis.

A further objective is to provide a system which includes an expert system for generating a diagnosis of a patient's cardiac condition and/or implantable device function based on information received from a pacemaker.

Another objective is to provide an automatic diagnostic system for a cardiac programmer in fuzzy logic architecture.

A programmer constructed in accordance with this invention includes a diagnostic circuit consisting of a memory for storing data, a fuzzification circuit and a fuzzy logic expert system. The fuzzy logic expert system takes numerical data that is telemetered from the pacemaker. A fuzzification process is used by the fuzzification circuit to translate the data into symbolic variables. A set of rules is then used to derive a diagnostic prognosis from the data. The rules mimic the thought processes and analysis employed by clinicians by translating the data into a symbolic and logic domain.

This invention speeds up the process of analizing the data and assist in interpretation by clinicians. The benefits of this invention has the advantage of naturally "mimicking" a clinician's thought process by translating numerical values into something linguistic and then making a diagnosis using knowledge obtained from clinicians. Thus, an automatic interpretation of the logged data is provided to save the clinician time and effort.

Some of the unique features are of this system are:

1. The use of fuzzy logic which allows a natural translation of numerical values from telemetered data for implantable devices.

2. The interpretation of telemetered data by utilization of expert systems rules (which allows knowledge from clinicians to be built into the system) for implantable devices.

3. Automatic interpretation of data logging.

BRIEF DESCRIPTION OF THE DRAWINGS

FIG. 3 shows a block diagram of the fuzzy logic analysis circuit in accordance with this invention;

FIGS. 4A–4D shows the fuzzification process of converting percent heart rate histogram into low, normal, and/or high heart rates membership functions;

FIG. 7 pictorially demonstrates the complete interpretation process from raw data logging data to a diagnostic conclusion.

DESCRIPTION OF THE PREFERRED EMBODIMENT

Figure 1:
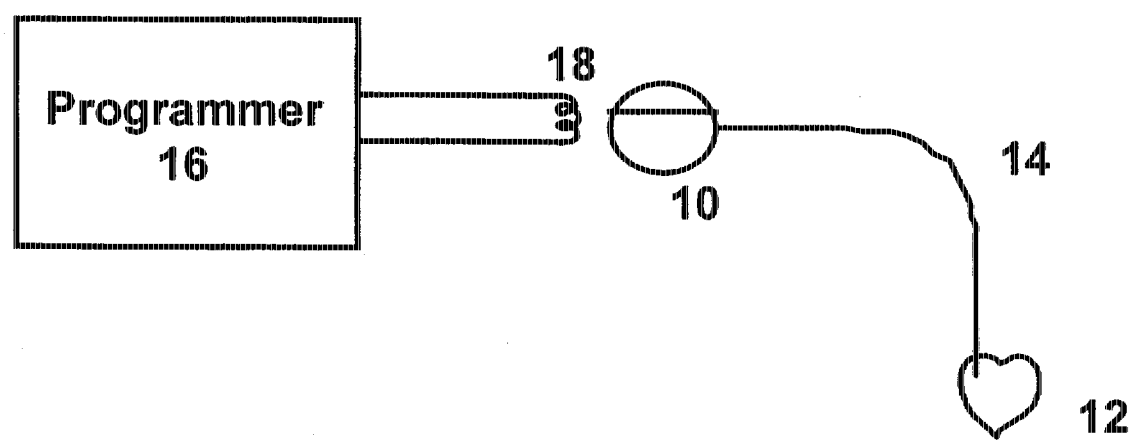
FIG. 1 shows a diagrammatic view of a programmer according to this invention in communication with a pacemaker.
Figure 2:
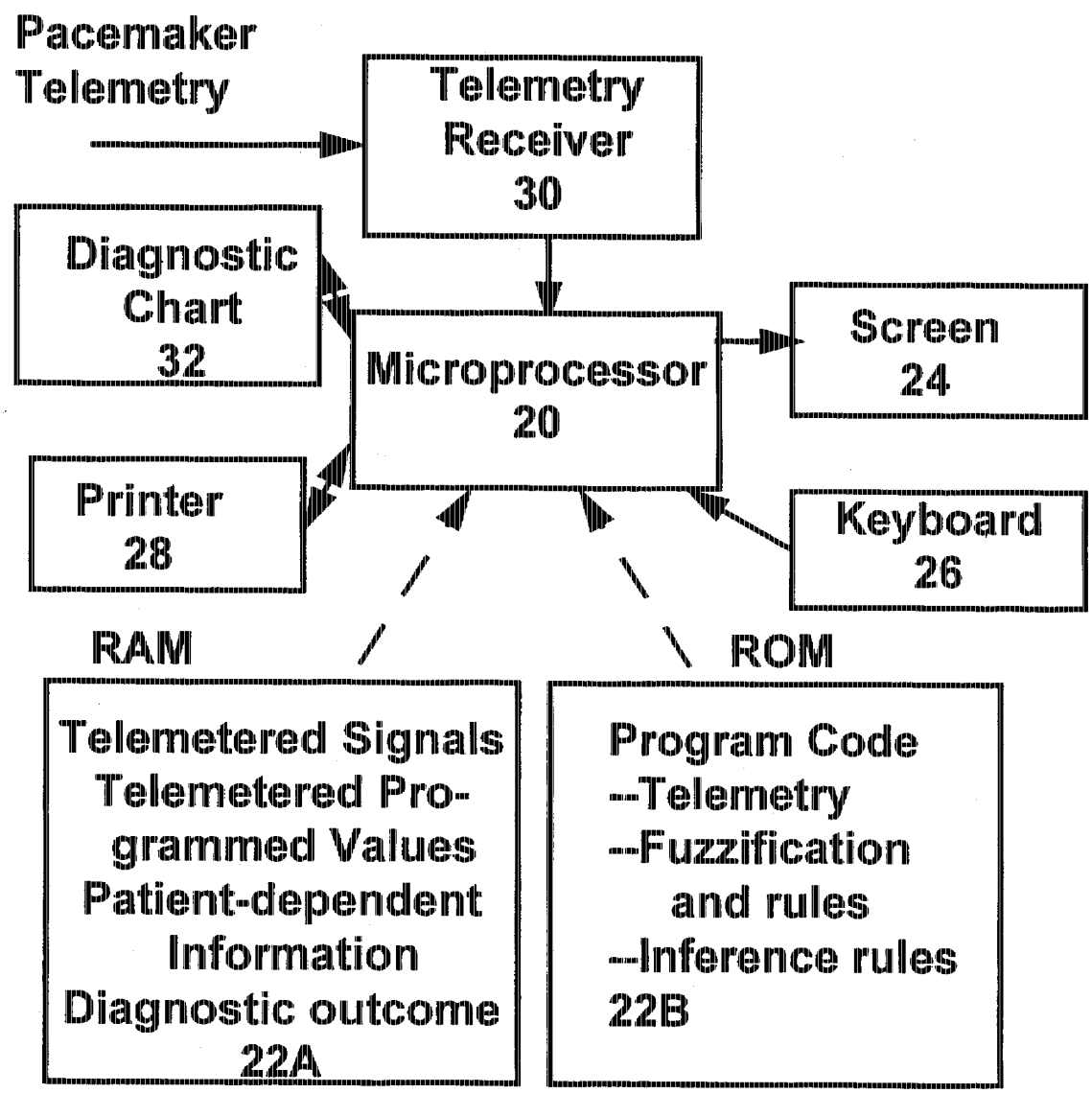
FIG. 2 shows a block diagram of the programmer of FIG. 1.

Referring first to FIGS. 1 and 2, typically an implanted pacemaker 10 senses intrinsic cardiac beats in heart 12 and generates pacing pulses on demand via leads 14. After implantation, or during subsequent followup visits, the operation of the pacemaker 10 is monitored by a programmer 16 through a wand 18. The wand 18 is used to establish telecommunication with the pacemaker 10 to exchange telemetry data.

As seen in detail in FIG. 2, the programmer 16 includes a microprocessor 20 in communication with a RAM 22A and a ROM 22B, a display 24, a keyboard 26, and optional printer 28. Data is exchanged through wand 18 via a telemetry circuit 30. Importantly, the programmer 16 further includes a diagnostic circuit 32 for performing diagnosis on the patient's heart 12 and for providing an appropriate prognosis to the clinician. In FIG. 2 circuit 32 is shown as a separate circuit. it being understood that in actuality, this circuit is preferably implemented by software in the microprocessor 20.

Referring to FIG. 3, the diagnostic circuit 32 contains five main components: a first information storage or memory 34 used for storing telemetry data, a fuzzification circuit 36, an inference engine 38 which includes the FAM 46 and a second memory 40 holding a set of expert rules. Together these last two components form a rule based fuzzy control system 42 defining a symbolic domain. Circuit 32 further includes a last element: a defuzzification circuit 44.

The information storage memory 34 accepts all telemetrically transmitted information associated with the pacemaker 10 for a predetermined time period, including programmable parameter values, automatic mode switching episode numbers, heart histograms, event histograms, trends and intracardiac ECG (electrocardiogram) and MTE (marker timing event) snapshots and stores the information for analysis.

The fuzzification circuit 36 processes the telemetrically received information and translates the telemetered data into symbolic variables as described more fully below.

The inference engine 38 utilizes results from the fuzzification circuit 36, the expert system knowledge base stored in memory 40, and the pacemaker and patient-specific information, that is normally either prestored or entered during the consultation, to derive a diagnostic statement or prognosis. It should be understood that diagnosis statement is dependent to the extent on the data base and set of expert rules provided for the inference engine 38. For example, if only a one dimensional heart rate histogram information is received from the pacemaker 10, then the diagnostic conclusion might not be as specific as if a two dimensional heart histogram was received. However, the expert system can incorporate additional information for a more specific conclusion.

The information storage memory 34 is used to store the following information:

(1) Administrative data including patient and pacemaker specific information such as: patient name, physician name, indications for pacing/implantable devices, relevant diseases, implant lead manufacturer, lead model, lead serial number, lead implant date, date of last program, last program update, etc.

(2) Programmed parameters required for the operation of the pacemaker 10, such as: mode, lead polarity, sensing, pacing and defibrillation thresholds, rates, AV interval, mode switching threshold, sudden rate drop response, sensor-related parameters, VT rate, etc.

(3) Long term information such as: date of last follow-up, cell impedance, longevity of battery, etc.

(4) Counters for specific events, such as: Percent paced (atrial or ventricular), premature ventricular contraction count, noise statistics (atrial and ventricular), pacemaker mediated tachycardia episodes, ventricular tachycardia episodes, automatic mode switching episodes, SSI, AV, and VA hysteresis, etc.

(5) Histograms for various events, such as: heart rate, atrial rate, sensor indicated rates, heart rate 2-D (event), mode switching duration, etc.

(6) Trends (variable time frame snapshots): heart rate, atrial rate, sensor-indicated rate, pacing sequence, mode switching, etc.

(7) A typical intracardiac electrogram with and without marker channels.

The fuzzification process involves receiving the information from the pacemaker and translating it into a symbolic membership function for use by the expert system. The fuzzification procedure can best be described by the following examples:

One important parameter which is useful in diagnosing a pathological condition is a fuzzy logic quantification of a patient's heart rate. This operation may be performed as follows. FIG. 4A shows a typical heart rate histogram for a patient. For example, according to FIG. 4A, this patient's heart rate was at 70 bpm for 30% of the time. In FIG. 4B a graph is shown for the high-rate-bin membership function. According to this function, rates below 100 bpm are excluded, rates above 120 bpm are included, and rates in between 100 and 120 bpm are classified based on a straight line function shown. FIG. 4C shows, based on the histogram of FIG. 4A, the percentages for each of the high bins for rates 110–150. These bins having been identified as the high bins by the function of FIG. 4B.

Using similar membership functions for bins associated with low and normal rates, three separate membership functions are then derived, as functions of cumulative percentages. FIG. 4D shows the membership function for the high bins related to cumulative percentages. This FIG. 4D shows that with the high bins (as defined in FIG. 4B) 1% or less of cardiac events occurred at low rates, as indicated by partition A. The spread of normal cardiac events is shown by partition B, while the percentages of high rate cardiac events are indicated by partition C. Thus, of all the cardiac events in the high rate bins at the 6% percentile value, 20% are attributable to high rate events and 80% are attributable to normal rate events.

The translation of a heart histogram into a heart rate membership function may be expressed mathematically as:

$$\text{Percent Time in High Bins} = \Sigma_{all\ bins}(\text{Percent\_of Rate in Bin i})*(\mu(\text{Bin i}))$$

Thus, a 6% heart rate in high bins would have 80% membership function in "Normal" and 20% in "High".

Figure 5:
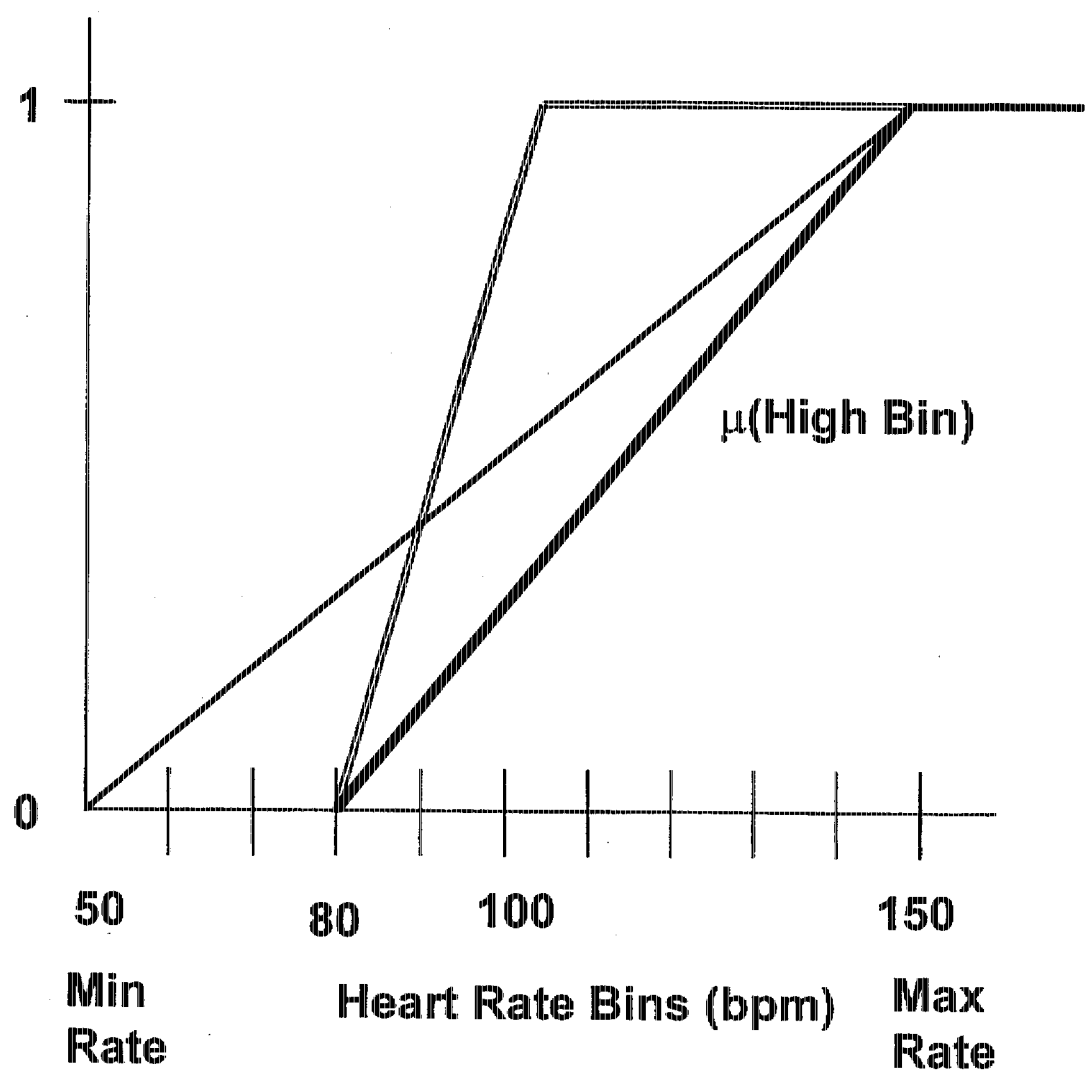
FIG. 5 shows alternative high rate bin definitions to the one shown in FIG. 4B.

Other possible membership functions similar to FIG. 4B is shown in FIG. 5.

A second example of fuzzification is shown below where one would like to obtain a function indicative of a higher or lower heart rate than the Atrial Rate based on histograms of the atrial rate as well as the heart rate. First, a numerical value difference is calculated from the following formula:

$$\text{Difference} = \Sigma_{all\ High\ Bins}((\%\ \text{of Heart Rate in Bin i}) - (\%\ \text{of Atrial Rate in Bin i}))*(\mu(\text{Bin i}))$$

Figure 6:
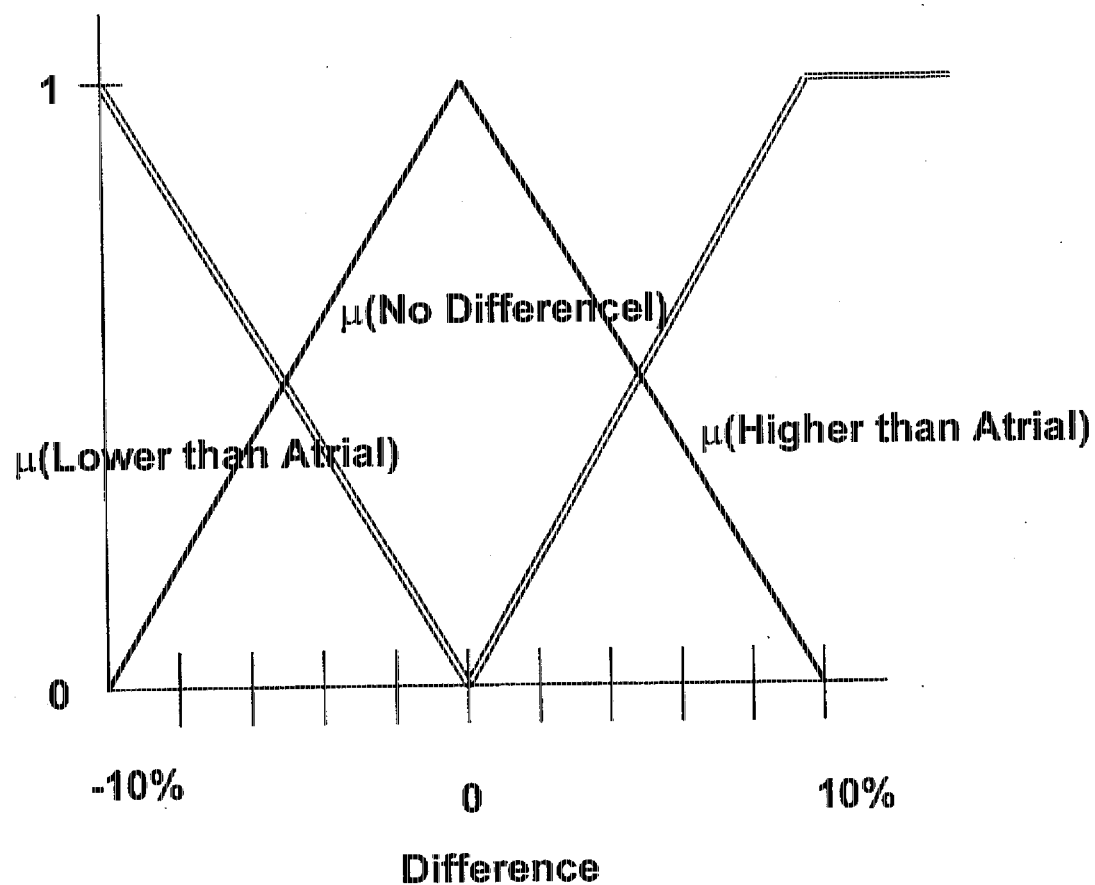
FIG. 6 shows the fuzzification process of converting the difference between two heart rate distributions into a function illustrative of ventricular heart rate distribution as it relates to the atrial heart rate distribution by membership functions.

Then the numerical value is inputted into the membership function defined in FIG. 6 and results (Lower, No Different, or Higher) can be outputted by circuit 36.

The expert system takes the fuzzification outputs of circuit 36, the patient-specific information from the RAM 20A, as well as the knowledge base to reach a diagnosis for the patient.

The knowledge base is obtained from expertise from experienced clinicians in pacemaker/implantable devices follow-up and troubleshooting. Normally, it is expressed as an if-then statement. Examples of the rules are shown below.

Many pacemakers are provided with a program which monitors specific cardiac functions and under certain conditions, the program switches from a mode in which the pacing rate is derived from a metabolic demand parameter to an AMS (automatic mode switching) mode in which a preset pacing rate which is independent of said metabolic demand parameter. Then, the conditions which triggered the AMS mode are no longer met, the pacemaker returns to its MIR (metabolic indicate rate) mode. One such pacemaker is described in U.S. Pat. No. 5,441,523.

In the present invention, the number of AMS (NAMS) episodes is counted in a counter included in the RAM 20A. This number NAMS and other parameters used in the following rules.

From Counters such as Number of Mode Switching (AMS) episodes:

1. If NAMS is Too High Then AMS Rate Change Needed or AMS Counter Change Needed or Atrial Fibrillation or Noise Sensing.

Other counters are used to count the number of atrial and ventricular noise episodes.

2. If Number of Atrial or Ventricular Noise Episodes Too High Then Atrial Oversensing or Ventricular Oversensing or Atrial or Ventricular Tachyarrhythmias Possible.

As previously stated, the RAM 20A is used to store cardiac histograms. The following rules can be derived from these histograms either directly or by comparing one histogram with another.

1. If Rate High Then Tachycardia Occurrence or Noise Sensing or Oversensing.

2. If Rate High and Mode Rate-responsive Then Rate Response Parameters Set too High.

3. If Rate Low and Mode Non-Rate-responsive and Patient Active Then Patient Chronotropically Incompetent.

4. If Rate Low Then Patient in Bradycardia Possible.

5. If Rate Lower than Atrial Rate Then Ventricular Undersensing or Atrial Oversensing or Atrial Tachyarrhythmia Possible.

6. If Rate Lower than Sensor Indicated Rate Then Patient is Chronotropically Incompetent or Rate Response Parameters set too High.

From 2-D Heart Histograms (Event Histograms) that stratify rate by pacing sequence (Indicated by a sequence of two letters: A=Paced Atrial Event, P=Sensed Atrial Event, V=Paced Ventricular Event, R=Sensed Ventricular Event, e.g. AV=Paced Atrial Event and Paced Ventricular Event):

1. If High Percent of Events in AR or AV Then Atrial Undersensing Possible.

2. If High Percent of Events in PV and AV Then Ventricular Undersensing Possible or AV Delay Too Short Possible.

3. If High Percent of Events in PV Then Atrial Oversensing Possible.

4. If High Percent of Events in PVCs Then Ventricular Oversensing Possible or PVCs Present.

5. If PV or PR Low Then Patient Chronotropically Incompetent.

6. If High Percent of Events in AV or PV and Patient Has No AV Block Then AV Delay Not Programmed Correctly.

7. If PV and PR High and Patient Taking Beta-blocker Drugs Then Inadequacy of Drug in Controlling Rate Possible.

From Trends and Snapshots:

If Rate Stays at Programmed Upper Rate Then Pacemaker Mediated Tachycardia Possible.

In general, the inference engine 38 considers all available information and arrives at a conclusion of potential problems and their associated causes. There are various algorithms for intelligently arriving at a conclusion. The usual method of inference is backward-chaining, where the algorithm starts with a goal or conclusion and searches backward into the knowledge base for rules and information that would be applicable to the particular conclusion. If the requisite information is not stored in the knowledge base, the expert system requests additional information sufficient to reach a diagnosis.

More specifically, the fuzzy expert system of FIG. 3 generates a conclusion of potential problems and associated causes based on the available patient datalog information in combination with the rules from memory 40. Fuzzy logic techniques for mathematically processing the information through the knowledge base to arrive at a conclusion are described for example by Mendel (see Mendel, J. M. "Fuzzy Logic Systems for Engineering: A Tutorial" IEEE Proceedings, 83(3):345-377 March 1995.

In the present system, the inference engine 38 includes fuzzy association memories 46 (FAMs) (see Kosko B. "Neural Networks and Fuzzy Systems" pp. 299-337, Prentice Hall Inc., Englewood Cliffs, N.J., 1992. These memories receive the input information in the form of fuzzy variable vector A and outputs a conclusion vector B using a matrix M using the relationship:

$$A*M=B$$

where * is a vector operator.

The expert rules listed above, or more properly the probabilities associated therewith defines the elements of matrix M. More specifically, each element Mij of matrix M is a probability relating probabilistically one input element, cause or symptom, i.e., $a_i$ leading to a pathological conclusion bj.

The vector operation * may be, for example one of a several fuzzy vector multiplication such as:

$$bj=\max_{(1 \leq j < n)} \min(a_i, m_{ij})$$

Preferably, however, the operator * is the $p_{13}$ or multiplication combination defined as:

$$bj=p_{13} \text{ or } 1 \leq i \leq u(a_i \text{ mij})$$

Where in general $P_{13}$ or $(a,b)=a+b-ab$

In this manner, evidence from different rules can be generated.

Once this vector A is generated by the engine 38, it is fed to the defuzzification circuit 44 to generate a single output, i.e., a conclusion or prognosis. Several such defuzzification techniques are discussed in the Mendel article. However, since the present invention involves probabilistic considerations, the defuzzification circuit 44 is preferably implemented such that it selects either the symptom probability $b_j$ from the vector B with the highest probability or, if $b_j$ is below a certain threshold, it may select two or three such symptoms with probability values attached to each.

In order to explain this process, reference is made to FIG. 7 which show respectively representative fuzzification functions for ventricular % ventricular pacings (i.e., the number of cardiac events which include a ventricular pacing pulse), and the percentage of premature ventricular contractions (PVC).

Thus, the two variables of interest are:

$a_1$: % of ventricular pacing and $a_2$: % of premature ventricular contraction.

These two variables represent two symptoms which point to specific pathological and/or pacemaker problems such as ($b_1$) ventricular oversensing or ($b_2$) ventricular tachycardia (VT). More particularly, the expert system has previously identified the following probability coefficients:

$$M_{11} \quad M_{12}$$
$$M_{21} \quad M_{22}$$

Where $M_{11}$ is the probability=ventricular oversensing associated with low percentage of ventricular pacing, $M_{12}$ is the probability of VT associated with low percentage of ventricular pacing, and so on. Thus, the problem vector B is related to the symptoms A as follows:

$$\begin{bmatrix} a1 \\ a2 \end{bmatrix} o \begin{bmatrix} M_{11} & M_{12} \\ M_{21} & M_{22} \end{bmatrix} = \begin{bmatrix} b1 \\ b2 \end{bmatrix}$$

Figure 8:
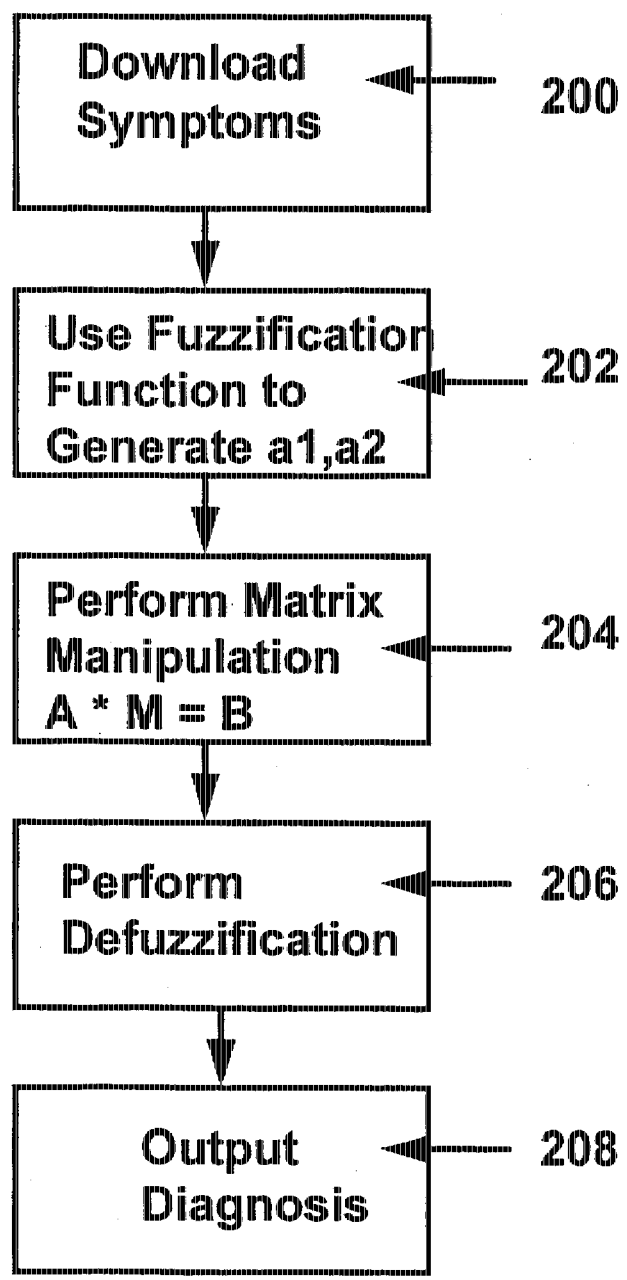
FIG. 8 shows the diagnostic steps for FIG. 7.

A diagram using these relationships is described in FIG. 8. Suppose that a patient comes into the office of a doctor and complains that he is not feeling well. The doctor couples the pacemaker to the diagnosis device described. The diagnosis device receives information from the pacemaker indicating that for this patent the % of ventricular pacing is 0% and a PVC counter indicates 5% (step 200).

In step 202, the fuzzification functions of FIGS. 7a and 7b, are used to determine the values of $a_1$ and $a_2$.

From FIGS. 7a, 7b it can be seen that $a_1=1$, and $a_2=0.44$ (step 202). Next, in step 204, the matrix calculation is performed. For the values given above, the calculations are as follows:

$$\begin{bmatrix} 1 \\ 0.44 \end{bmatrix} o \begin{bmatrix} 0.25 & 0.25 \\ 0 & 0.25 \end{bmatrix} =$$

$$\begin{matrix} P\_OR\,((1)(0.25),(.44)(.25)) & P\_OR\,(.25,.11) \\ P\_OR\,((1)(0),(.44)(.25)) & P\_OR\,(0,.11) \end{matrix} = \begin{matrix} 0.33 \\ 0.11 \end{matrix}$$

The operation $P_{13}OR$ was defined above. This calculation indicates that there is 33% chance that the patient's problems stem from ventricular oversensing and an 11% chance that he is suffering from VT. In step 208 a defuzzification process is followed. For example, assuming that 33% is higher than a preset threshold, a diagnosis is provided that the pacemaker's sensory threshold is too sensitive and should be reset.

Of course, it should be understood that this is a simplistic example provided for a better understanding of the invention. In actuality, vector A could have up to 60 elements, and matrix M is a relatively large matrix of for example 60×70 elements.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

We claim:

1. A cardiac diagnostic device comprising:

a transceiver for receiving information from an implantable cardiac device;

a first memory for storing a plurality of expert rules correlating patient symptoms and cardiac device operations to cardiac problems;

a fuzzy logic circuit for receiving said information, said fuzzy logic circuit being arranged to manipulate said information to generate fuzzy logic parameters in accordance with a preset fuzzy logic functions; and an inference circuit for analyzing said fuzzy logic parameters in accordance with said rules to generate a prognosis, said prognosis identifying one of a pathological and cardiac implant problem based on said rules.

2. The device of claim 1 further comprising a second memory for storing said information, said information including cardiac implant-specific and patient-specific data.

3. The device of claim 1 wherein said analyzer generates a plurality of intermediate prognosis signals said device further comprising a defuzzification circuit for generating an output prognosis signal based on said plurality of intermediate prognosis signals.

4. The device of claim 3 wherein each of said intermediate prognosis signals is associated with a probability value indicative of a probability of said intermediate prognosis, and wherein said defuzzification circuit selects one of said intermediate prognosis signals as said output prognosis signal in accordance with said values.

5. A cardiac diagnostic device for generating a prognosis identifying a specific cardiac malfunction selected from a group of pathological problems or cardiac implant problems, said device comprising:

a receiver for receiving a plurality of input parameters from a cardiac implant, said input parameters being indicative of operational and patient specific characteristics;

a fuzzification circuit for generating an input vector from said parameters based on a set of fuzzification functions, each vector including a plurality of values for symptoms;

a memory for holding a plurality of inference coefficients based on statistical information, each coefficient representing a probabilistic relationship between a particular symptom and a corresponding cardiac malfunction, said coefficients defining a multivalued array; and an inference machine for performing a vector operation between said input vector and said array to generate a prognosis vector, said prognosis vector including a plurality of probabilistic values for a set of cardiac malfunctions.

6. The device of claim 5 further comprising a defuzzification circuit for generating an output prognosis signal based on said prognosis vector values.

7. The device of claim 6 wherein said defuzzification circuit selects the prognosis from said vector which has the highest probability.

* * * * *